(12) United States Patent
Lee-Gardner

(10) Patent No.: US 11,950,939 B2
(45) Date of Patent: Apr. 9, 2024

(54) SANITARY MEDICAL SURFACE DEVICE

(71) Applicant: Lisa Lee-Gardner, Saint Martinville, LA (US)

(72) Inventor: Lisa Lee-Gardner, Saint Martinville, LA (US)

( * ) Notice: Subject to any disclaimer, the term of this patent is extended or adjusted under 35 U.S.C. 154(b) by 31 days.

(21) Appl. No.: 17/868,433

(22) Filed: Jul. 19, 2022

(65) Prior Publication Data
US 2024/0024060 A1      Jan. 25, 2024

(51) Int. Cl.
*A61B 50/31*   (2016.01)
*A61B 50/00*   (2016.01)
*A61B 50/30*   (2016.01)

(52) U.S. Cl.
CPC ...... *A61B 50/31* (2016.02); *A61B 2050/0056* (2016.02); *A61B 2050/3008* (2016.02); *A61B 2050/3011* (2016.02); *A61B 2050/311* (2016.02)

(58) Field of Classification Search
CPC ............ A61B 2050/0056; A61B 50/31; A61B 2050/3008; A61B 2050/3011
USPC ......................................................... 206/570
See application file for complete search history.

(56) References Cited

U.S. PATENT DOCUMENTS

| | | | |
|---|---|---|---|
| 9,072,543 B2 * | 7/2015 | Miller | A61B 17/3472 |
| 11,065,074 B2 * | 7/2021 | Holstein | A61F 17/00 |
| 11,278,367 B1 * | 3/2022 | Diaz | A61B 90/39 |
| 2008/0141700 A1 * | 6/2008 | Fuchs | F25D 3/08 206/570 |
| 2011/0297147 A1 * | 12/2011 | Lick | A61B 50/31 128/202.16 |

* cited by examiner

*Primary Examiner* — Steven A. Reynolds

(57) ABSTRACT

A sanitary medical surface device is provided having a first portion with a first outer surface and a first inner surface. The first inner surface may have a first work surface and the second inner surface may have a second work surface. The device may further utilize a first channel depression formed into the first inner surface such that the first channel depression may be disposed along first perimeter edges of the first work surface. The device may utilize a first raised lip disposed along third perimeter edges of the first inner surface along with one or more stabilization structures disposed upon the first outer surface.

15 Claims, 7 Drawing Sheets

SANITARY MEDICAL SURFACE DEVICE

BACKGROUND OF THE INVENTION

The in-home care services industry in the US was estimated to generate annual revenue of nearly 100 billion dollars in 2020 based upon an existing 15 million in-home patients requiring roughly 600 million in-home patient visits each year. The most common ailments requiring in-home care services are heart disease, diabetes, cerebral vascular diseases, physical disability and rehabilitation.

Patients who require frequent, often daily, medical care would like to have the freedom of living in their own homes without the need of traveling each day into a medical facility to receive their medical care. Such patients may find each of these needs satisfied by utilizing in-home medical care services. Specifically, the in-home nurse provides in-home medical services to a patient which relieves the patient of the burden of travel while allowing them to enjoy the freedom of living in their own homes full time.

Inherent to an in-home care nurse's job is travel to and between each of the various in-home patient sites. Therefore, it is onerous for the nurse to have to carry too much medical equipment and supplies to and between each patient site. Further, the equipment and supplies that are required for the nurse's work are ideally easily transported in an easily carried portable device. Consequently, it would be advantageous to provide a portable work device that holds all necessary equipment and supplies while also being easily transported between work sites.

When traveling between each work site, the in-home care nurse typically encounters a variety of terrain, modes of transport and length of travel. Any equipment and supplies being carried by the nurse will need to be robustly secured against such environmental circumstances during travel. Further, many items of medical equipment are not robust to rough transport on a bumpy road or accidental collisions with ground surface or other objects during transport. Therefore, it would be advantageous to provide a device that may securely retain any medical equipment and supplies therein without risk of becoming structurally compromised in the event of a collision or like acute impact.

Another concern for a traveling in-home care nurse is the transport of medical waste generated from the in-home care of the patient. Often, such medical waste cannot be disposed of in the patient's home and, therefore, must be transported according to state and federal medical waste regulations out of the patient's home and into a proper medical waste receptacle. Consequently, it would be advantageous to provide a device that is capable of safely retaining medical waste therein that complies with state and federal regulation by not allowing leakage of any fluid medical waste during transport.

Additionally, when an in-home care nurse is administering medical care to the in-home patient, the nurse may encounter a wide variety of environments within which to operate. For instance, some patient homes may have ample clean flat surfaces upon which to perform nurse functions while other patient homes may be less suitable for such work. It would be useful to provide a device that comprises a sanitary medical surface upon which the nurse may perform their work duties without risk of contamination or spillage due to unsanitary and/or unstable work surfaces in the patient home. Specifically, it would be advantageous to provide a sanitary medical work surface that utilizes spill-protection structures along the perimeter or other portions of the work surface and utilizes stabilizing legs and pads underneath the work surface to ensure a flat stable work surface.

Further, given the number of patients a traveling in-home care nurse may see in a single day, the need to repeatedly sanitize their equipment and work surfaces can become burdensome and may lead to accidental contamination. Such contamination can cause serious injury or death in the patient or the nurse and so is a serious liability risk for a company employing thousands of in-home care nurses who each see handfuls of patients each day.

Therefore, it would be advantageous to provide a sanitary medical surface device that provides one or more sanitary fail-safe mechanisms providing disinfecting and/or anti-pathogenic characteristics such as, but not limited to, UV illumination elements, antimicrobial material coatings, antimicrobial impregnated materials and the like or any combination thereof.

DETAILED DESCRIPTION OF THE INVENTION

Figure 1:
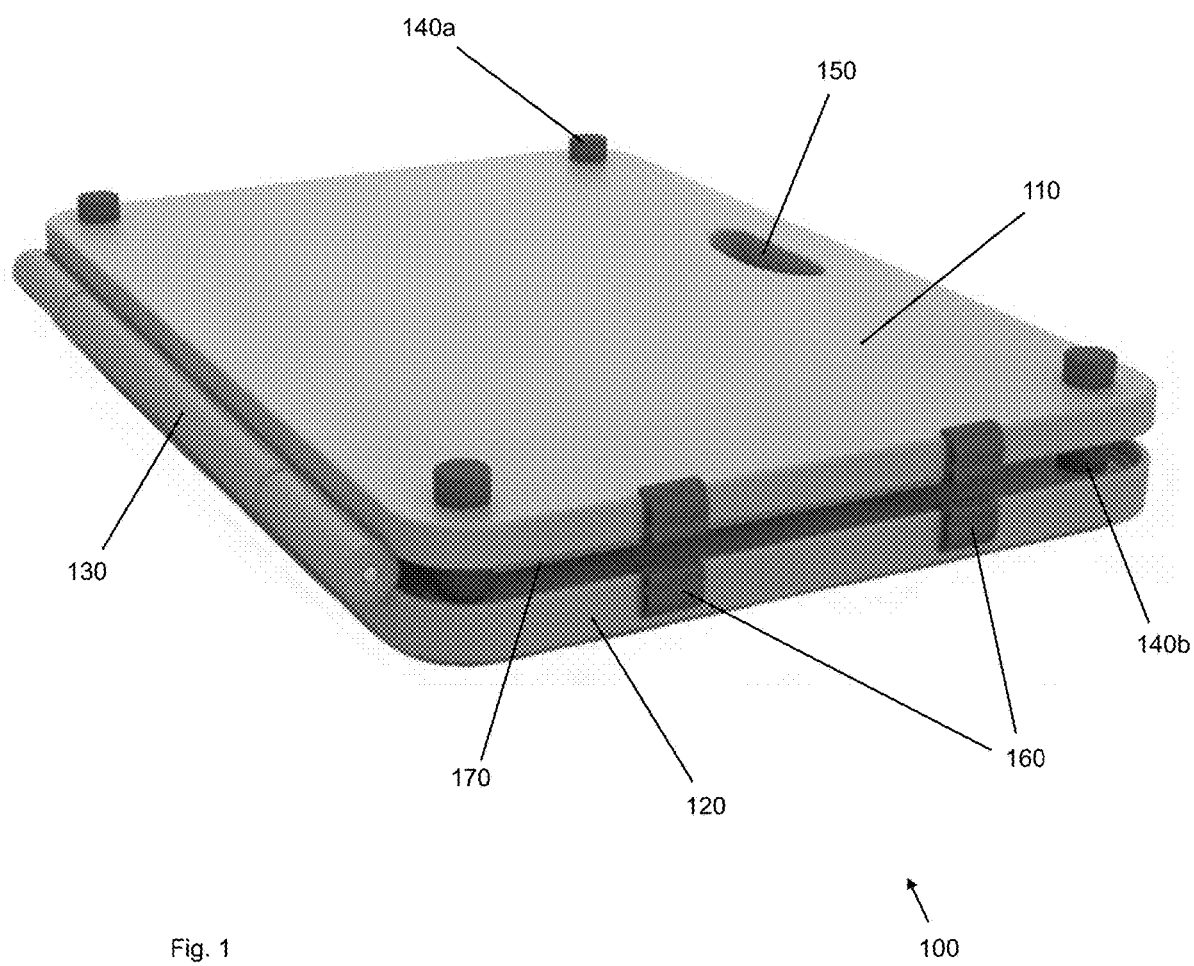
FIG. 1 illustrates a perspective view of a sanitary medical surface device in a closed configuration according to some embodiments of the present invention.

Before describing the present invention in detail, it is to be understood that the invention is not limited to any one of the particular embodiments, which of course may vary. It is also to be understood that the terminology used herein is for the purpose of describing particular embodiments only, and therefore is not necessarily intended to be limiting. As used in this specification and the appended claims, terms in the singular and the singular forms "a," "an," and "the" include plural referents unless the context clearly dictates otherwise. Thus, for example, reference to "a sanitary medical surface device" also includes a plurality of sanitary medical surface devices and the like.

In some embodiments, a sanitary medical surface device is provided comprising: a first portion, wherein the first portion comprises a first outer surface and a first inner surface, and the first inner surface comprises a first work surface and the second inner surface comprise a second work surface; a first channel depression formed into the first inner surface, wherein the first channel depression is disposed along first perimeter edges of the first work surface; a first raised lip disposed along third perimeter edges of the first inner surface; and one or more stabilization structures disposed upon the first outer surface.

In some embodiments, the first portion is a first half portion which is coupled to a second half portion via a first rotatable hinge; the second half portion comprises a second outer surface and a second inner surface; a second channel depression formed into the second inner surface, wherein the second channel depression is disposed along second perimeter edges of the second work surface; a second raised lip disposed along fourth perimeter edges of the second inner surface; and one or more stabilization structures disposed upon the second outer surface.

In some embodiments, the first rotatable hinge comprises a first hinge section and a second hinge section.

In some embodiments, the first rotatable hinge rotates the first half portion relative the second half portion through an angle of no more than 180 degrees.

In some embodiments, in a closed configuration, the first inner surface is disposed adjacent and parallel to the second inner surface and, in an open configuration, the first inner surface is disposed within the same plane as the second inner surface.

In some embodiments, a first portion of a handle cavity is disposed into the first outer surface and a second portion of the handle cavity is disposed into the second outer surface.

In some embodiments, the first inner surface or the second inner surface comprises a clip for retaining documents thereupon.

In some embodiments, the first inner surface or the second inner surface comprises a rounded retention depression formed therein.

In some embodiments, the first inner surface or the second inner surface comprises a panel covering a storage compartment.

In some embodiments, the panel is partially removable via one or more second rotatable hinges to provide access to the storage compartment.

In some embodiments, the removable panel forms a fluid-tight seal with the first inner surface or the second inner surface.

In some embodiments, the removable panel forms a flush surface with the first inner surface or the second inner surface.

In some embodiments, the panel is the first work surface or the second work surface.

In some embodiments, the first outer surface or the second outer surface comprises a panel covering a storage compartment.

In some embodiments, the first inner surface comprise a third channel depression and the second inner surface comprises a fourth channel depression.

In some embodiments, a first handle aperture is disposed through the first outer surface and the first inner surface and a second handle aperture is disposed through the second outer surface and the second inner surface.

In some embodiments, each of the first and second channel depressions comprise a shape that tapers down in a rounded path from the first and second inner surfaces, respectively, towards a rounded bottom portion of the first and second channel depressions, respectively.

In some embodiments, each of the first and second channel depressions comprise a shape that forms a 90 degree angle squared-edge with the first and second inner surfaces, respectively.

In some embodiments, a sanitary medical surface device is provided comprising: a first half portion and a second half portion coupled together via a first rotatable hinge, wherein the first half portion comprises a first outer surface and a first inner surface and the second half portion comprises a second outer surface and a second inner surface, and the first inner surface comprises a first work surface and the second inner surface comprise a second work surface; a first channel depression formed into the first inner surface, wherein the first channel depression is disposed along first perimeter edges of the first work surface; a second channel depression formed into the second inner surface, wherein the second channel depression is disposed along second perimeter edges of the second work surface; a first raised lip disposed along third perimeter edges of the first inner surface and a second raised lip disposed along fourth perimeter edges of the second inner surface; a first handle aperture disposed through the first outer surface and the first inner surface and a second handle aperture disposed through the second outer surface and the second inner surface, wherein a third channel depression is formed into the first inner surface and disposed around the first handle aperture and a fourth channel depression is formed into the second inner surface and disposed around the second handle aperture; and one or more stabilization structures disposed upon either or both of the first outer surface and the second outer surface.

In some embodiments, a sanitary medical surface device is provided comprising: a first half portion and a second half portion coupled together via a first rotatable hinge, wherein the first half portion comprises a first outer surface and a first inner surface and the second half portion comprises a second outer surface and a second inner surface, and the first inner surface comprises a first work surface and the second inner surface comprise a second work surface; a first channel depression formed into the first inner surface, wherein the first channel depression is disposed along first perimeter edges of the first work surface; a second channel depression formed into the second inner surface, wherein the second channel depression is disposed along second perimeter edges of the second work surface; a first raised lip disposed around the first channel depression and a second raised lip disposed around the second channel depression; and a plurality of stabilization structures disposed upon each of the first outer surface, the first inner surface, the second outer surface and the second inner surface.

Exemplary embodiments of the present invention are illustrated in the accompanying figures. As shown in FIG. 1, a perspective view of a sanitary medical surface device 100 in a closed configuration is provided. The sanitary medical surface device 100 may comprise a first half portion 110 and a second half portion 120 coupled together via a rotatable hinge 130. Each of the first and second half portions 110, 120 may comprise a first side surface and an opposing second side surface. The rotatable hinge 130 may be utilized to iteratively manipulate the first and second half portions 110, 120 between open and closed configurations as desired by a user of the sanitary medical surface device 100.

Each of the first and second side surfaces of both of the first and second half portions 110, 120 may comprise one or more stabilization leg pads where the first side surface of the first and second portions 110, 120 may comprise a first set of stabilization pads 140a and the second side surface of the first and second portions 110, 120 may comprise a second set of stabilization pads 140b. When in the closed configuration as shown in FIG. 1, the second set of stabilization pads 140b of both first and second half portions 110, 120 may be disposed adjacent or in contact with one another in order to provide an elastic stopping point for rotation of the hinge 130 when placing the device 100 into the closed configuration. When in the open configuration (see FIG. 2), the first set of stabilization pads 140a of both first and second half portions 110, 120 may be disposed adjacent or in contact with one or more ground surfaces.

The first and second half portions 110, 120 may each comprise an aperture formed therein that together form a handle 150 as shown in FIG. 1. The handle 150 may be defined by the apertures being aligned when the first and second half portions 110, 120 are disposed adjacent one another in the closed configuration. Each aperture may be fabricated into the body of first and second half portions 110, 120 and further may be disposed through both the first and second surfaces of both first and second half portions 110, 120 as shown in FIG. 1. The apertures may be shaped to conform to the shape of an in-home care nurse's fingers and palm for ease of transportation between patient work sites. Specifically, a first portion of each aperture closest to the outer perimeter of each first and second half portion 110, 120 may comprise a concave shape while a second portion furthest from the outer perimeter may comprise a convex shape to match the structural profile of the nurse's hand when gripping the device 100 by the handle 150 during transport.

The outer perimeter edge of each of the first and second half portions 110, 120 may comprise one or more clips 160 for retaining work items therefrom. Specifically, when working on a patient, space within the patient's home may be limited for the nurse to perform work. Therefore, the one or more clips 160 may be utilized to retain work items such as waste receptacle bags, IV reservoir bags, blood transfusion bags, nurse medical equipment and the like or any combination thereof. Given the proximity of the medical equipment storage area within the device 100 and the sanitary work surface provided by the device 100, the one or more clips 160 are advantageously coupled to side surfaces of the body of the device 100.

Additionally, the outer perimeter edge of each of the first and second half portions 110, 120 may comprise one or more antimicrobial illumination elements 170 disposed along an inner perimeter edge of at least one of the first and second half portions 110, 120. The one or more antimicrobial illumination elements 170 may take the form of an illumination element emitting radiation within the ultraviolet wavelength band. Specifically, the ultraviolet radiation band may comprise UV-A, UV-B and/or UV-C wavelength bands. Further, one or more UV LEDs emitting in a similar wavelength band may be utilized. Moreover, individual illumination elements may be utilized in series or a strip of illumination elements fabricated together upon a common substrate may be utilized to provide antimicrobial functionality for the device 100 between patient visits. For instance, upon finishing a first patient, the in-home care nurse may place the device 100 into the closed configuration which allows the antimicrobial UV light to sanitize the medical work surfaces contained on the interior of the first and second half portions 110, 120 when the device 100 is in the closed configuration.

Figure 2:
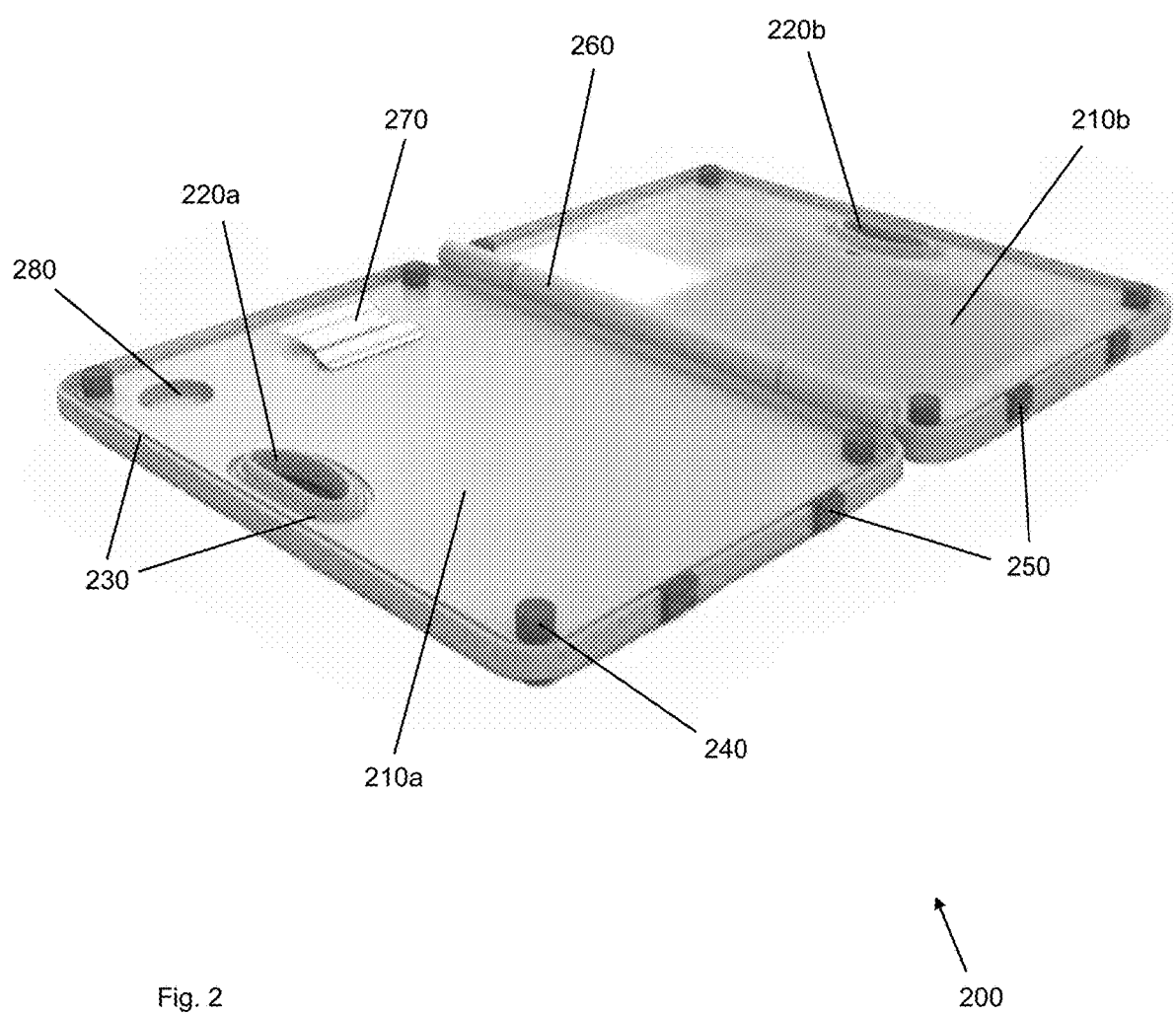
FIG. 2 illustrates a perspective view of a sanitary medical surface device in an open configuration according to some embodiments of the present invention.

As shown in FIG. 2, a perspective view of a sanitary medical surface device 200 in an open configuration is provided. The device 200 may comprise a first inner surface 210a and a second inner surface 210b arranged in the same plane and parallel one another in the open configuration. The first and second inner surfaces 210a, 210b are coupled together via a rotatable hinge 260 that allows the device 200 to transition between open and closed configurations.

Each of the first and second inner surfaces 210a, 210b comprise a handle aperture 220a, 220b disposed therethrough. Further, a perimeter fluid channel 230 may be disposed around the outer edges of each of the first and second inner surfaces 210a, 210b as well as the outer edge of each of the handle apertures 220a, 220b. The perimeter fluid channel 230 may be formed as a depression into the inner surfaces 210a, 210b so that any liquid runoff therefrom will be captured by the channel 230 and will not spill over the sides of the device 200 and thereafter contaminate the home of the patient that the nurse is treating. For instance, liquid medical waste may be handled upon the inner surfaces 210a, 210b during in-home care of the patient. Any spillage of such liquid medical waste could permanently contaminate the home furnishings that receive any of the spillage and pose as a health threat to those living in the home. Therefore, the perimeter fluid channel 230 may act as a key safety feature in preventing health risks for a patient receiving in-home medical care.

Additionally, each of the first and second inner surfaces 210a, 210b may comprise a plurality of stabilizing pads 240. While a single stabilizing pad 240 is illustrated in FIG. 2 as being disposed at each corner of each inner surface 210a, 210b, it is to be understood that one or more stabilizing pads 240 may be placed along any perimeter portion of the first and second inner surfaces 210a, 210b. Advantageously, FIG. 2 illustrates the stabilizing pads 240 at identical locations upon the first and second inner surfaces 210a, 210b. Thereby, when the device 200 is placed into the closed configuration then the stabilizing pads 240 will align and act as a stop for rotation of the hinge 260. Further, this configuration allows air to flow freely between first and second inner surfaces 210a, 210b during transport in the closed configuration which acts to further decontaminate the inner surfaces. Moreover, this configuration allows the one or more antimicrobial illumination elements 170 space to irradiate the inner surfaces 210a, 210b for further sanitization of the device 200 in the closed configuration and during transport.

Similar to FIG. 1, a plurality of clips 250 are illustrated in FIG. 2 along the outer perimeter edge of the device 200. These clips 250 may serve the same purpose as described with respect to FIG. 1. Structurally, the clips 250 may be spring-loaded pressure clips that robustly retain any item therein that the weight of the device 200 may carry when laid flat on a stable surface. Similarly, an inner surface clip 270 may be disposed upon one or more of the inner surfaces 210a, 210b in order to retain absorbent materials over the inner surface to further prevent spillage of liquid medical waste. Further, the inner surface clip 270 may be utilized to retain paperwork needed to be filled out by the in-home care nurse relating to the medical care to be provided to the in-home patient.

One or more of the first and second inner surfaces 210a, 210b may comprise a retention depression 280 formed into the surface thereof. The depression 280 may be utilized for a variety of purposes such as a cupholder, a liquid collection reservoir, a small item retention area, a metallic item retention area and the like or any combination thereof. In some embodiments, the depression 280 may comprise a magnetic element built into the bottom base portion thereof so as to retain therein any small metallic items like paper clips, safety pins, tacks, small metallic medical accessories and the like or any combinations thereof.

Figure 3:
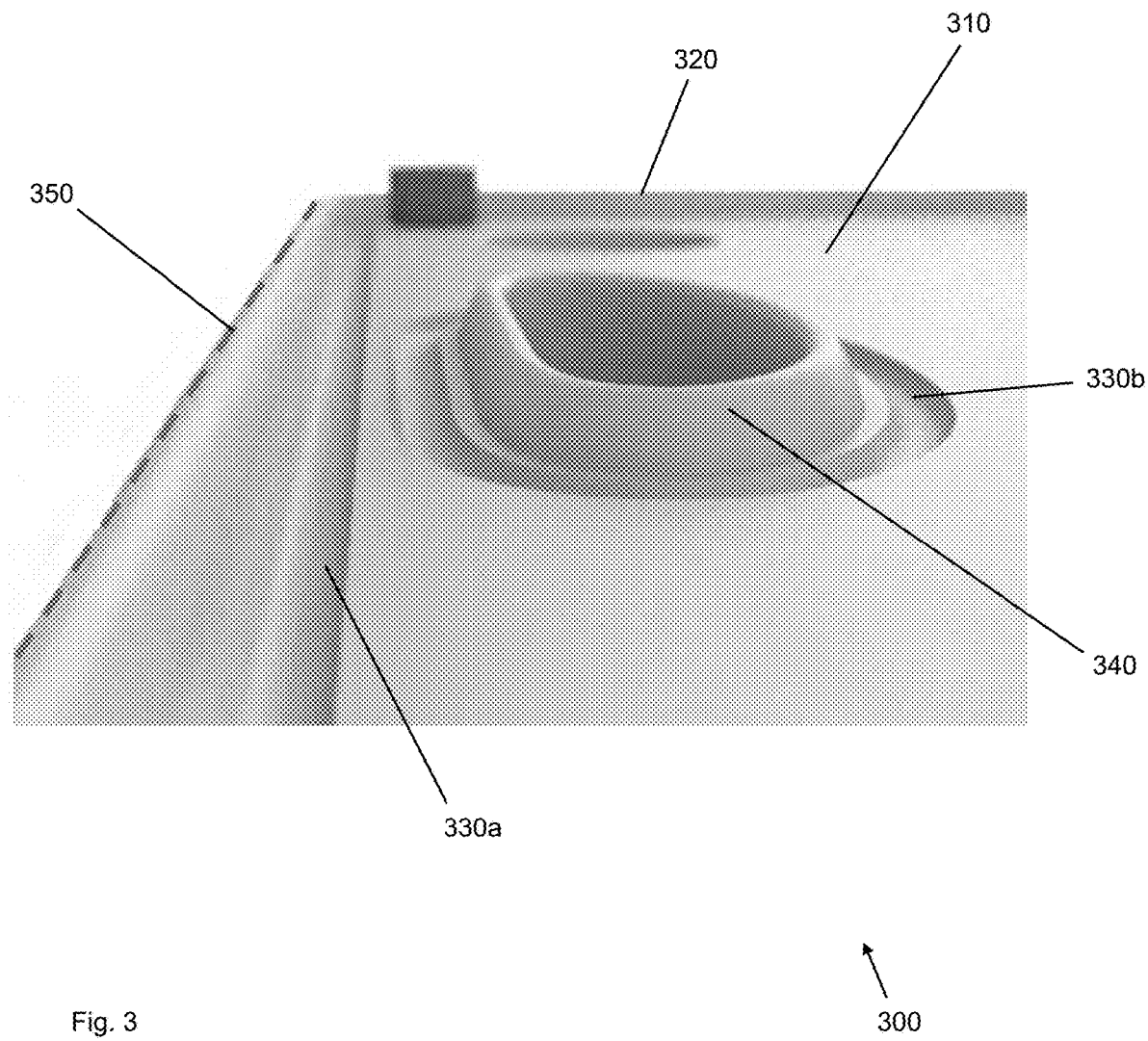
FIG. 3 illustrates a detailed view of an inner perimeter portion of a sanitary medical surface device in an open configuration according to some embodiments of the present invention.

As shown in FIG. 3, a detailed view of an inner perimeter portion of a sanitary medical surface device 300 in an open configuration is provided. The inner perimeter portion of the device 300 may comprise an inner surface 310 that at a perimeter portion comprises an outer lip 320 running along the entirety of the perimeter of the inner surface 310. Further, the inner surface 310 may comprise a perimeter fluid channel 330a formed into the inner surface and running adjacent the outer lip 320 along the entirety of the perimeter portion of the inner surface.

The perimeter fluid channel 330a may be formed into the inner surface 310 as a depression therein. Specifically, the channel 330a depression may have a shape that slowly tapers from the inner surface 310 towards to bottom-most portion of the depression as shown in FIG. 3. Alternatively, the channel 330a depression may have a shape that sharply drops in a vertical direction from the horizontal inner surface 310 at a near 90 degree angle and then tapers towards the bottom-most horizontal portion of the depression.

In either case, the bottom-most portion of the channel 330a may comprise a rounded u-shape so that any liquids retained therein are easily cleaned by the in-home care nurse. If the bottom-most portion of the channel 330a were to have a squared u-shape then it would be much more difficult to clean the entirety of the liquid out from the 90 degree corners of the squared u-shape. Similarly, the handle lip 340 forming the aperture of the handle may comprise a perimeter fluid channel 330b structured and purposed in a similar manner to that described with respect to the perimeter fluid channel 330a.

The handle lip 340 is illustrated in FIG. 3 as forming a handle aperture that comprises a planar straight shape nearest the outer lip 320 which then transitions into a convex shape farthest from the outer lip. Alternatively, the handle aperture may comprise a concave shape nearest the outer lip 320. In either case, the handle lip 340 is shaped to best universally accommodate the shape, contour and form factor of the average hand of an in-home care nurse. While the perimeter fluid channel 330b is illustrated in FIG. 3 as not directly adjacent the handle lip 340, it is understood that the handle lip may be fabricated to directly transition into the depression of the perimeter fluid channel 330b such that the handle lip and perimeter fluid channel 330b are arranged directly adjacent one another.

The outer lip 320 may further comprise one or more antimicrobial illumination elements 350 disposed therein or thereupon. The one or more antimicrobial illumination elements 350 may take the form of an illumination element emitting radiation within the ultraviolet wavelength band. Specifically, the ultraviolet radiation band may comprise UV-A, UV-B and/or UV-C wavelength bands. Further, one or more UV LEDs emitting in a similar wavelength band may be utilized. Moreover, individual illumination elements may be utilized in series or a strip of illumination elements fabricated together upon a common substrate may be utilized to provide antimicrobial functionality for the device 300 between patient visits. For instance, upon finishing a first patient, the in-home care nurse may place the device 300 into the closed configuration which allows the antimicrobial UV light to sanitize the medical work surfaces contained on the interior of the device 300.

In some embodiments, the antimicrobial illumination elements 350 may only be activated when the device 300 is placed into the closed configuration. Specifically, the rotatable handle discussed in reference to FIGS. 1 and 2 may comprise circuitry therein that activates the antimicrobial illumination elements 350 upon rotation beyond a threshold point into the closed configuration. Conversely, the rotatable handle circuitry may deactivate the antimicrobial illumination elements 350 upon rotation beyond a threshold point into the open configuration. In some embodiments, the rotatable handle circuitry may be coupled to the power source for the illumination elements 350 such that the circuitry creates an open circuit between the power source and the illumination elements 350 when the rotatable handle is rotated beyond a threshold point into the open configuration. Conversely, the circuitry may create an active closed circuit between the power source and the illumination elements 350 when the rotatable handle is rotated beyond a threshold point into the closed configuration.

Figure 4:
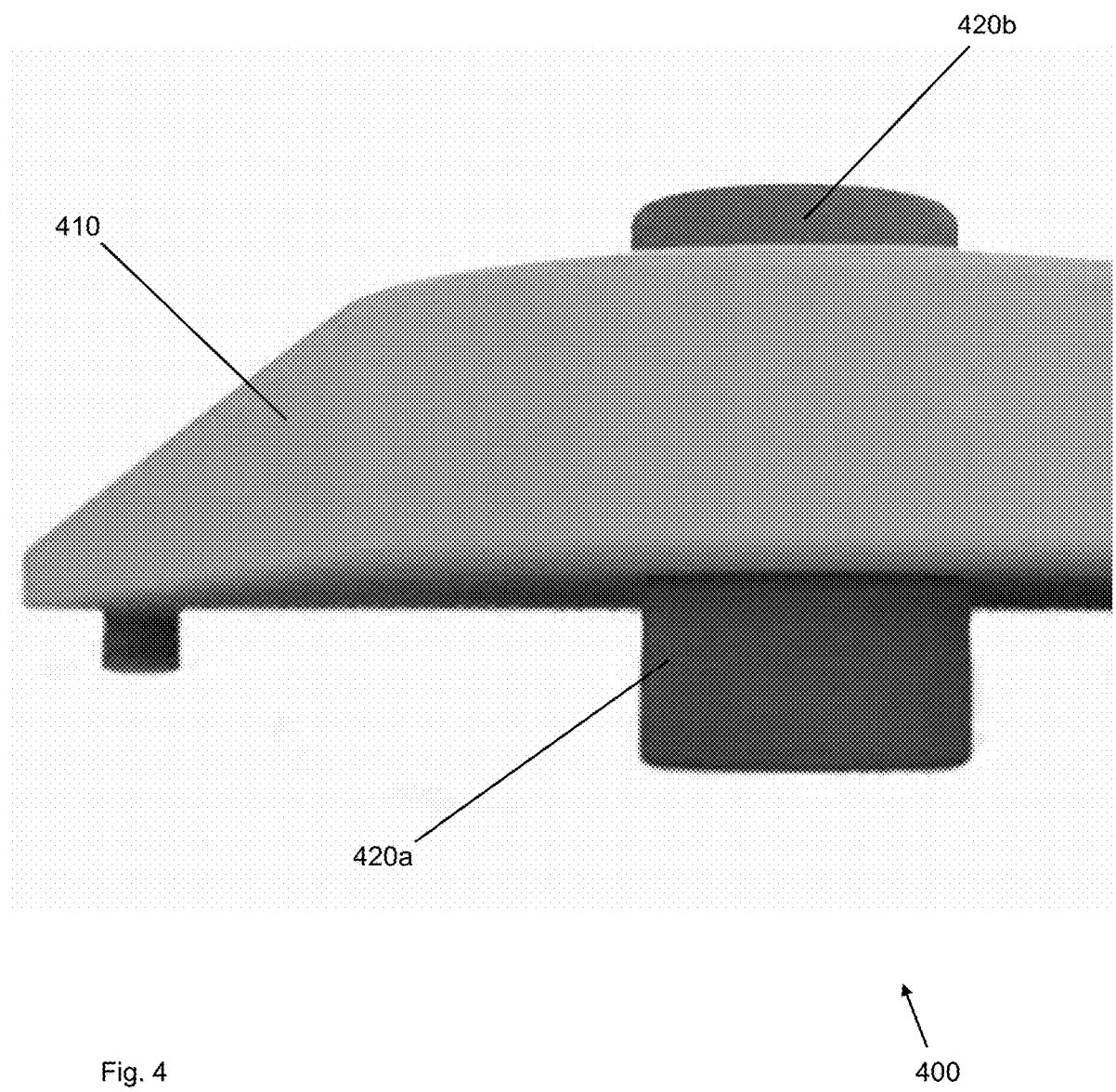
FIG. 4 illustrates a detailed view of an outer perimeter portion of a sanitary medical surface device in an open configuration according to some embodiments of the present invention.

As shown in FIG. 4, a detailed view of an outer perimeter portion of a sanitary medical surface device 400 in an open configuration is provided. The device 400 may comprise a work surface 410 having a first set of stabilization pads 420a disposed on the outer surface of the work surface 410 and a second set of stabilization pads 420b disposed on the inner surface fo the work surface 410. The first and second set of stabilization pads 420a, 420b may be vertically aligned with one another through the work surface 410 for ease of manufacture and assembly of the device 400.

In use, the stabilization pads 420a, 420b may be fabricated from a flexible high-coefficient of friction material such as, but not limited to, rubber polymers, foam polymers, silicone elastomers and the like or any combination thereof. Alternatively, the stabilization pads 420a, 420b may be fabricated from sturdy injection moldable polymer materials which then may have a material coating or layer applied having a high-coefficient of friction with common surface materials. In either event, the stabilization pads 420a, 420b should be robust under load and non-absorbent so as to remain sanitary when liquid medical waste is incident thereupon by providing an easy to clean surface material between uses.

Figure 5:
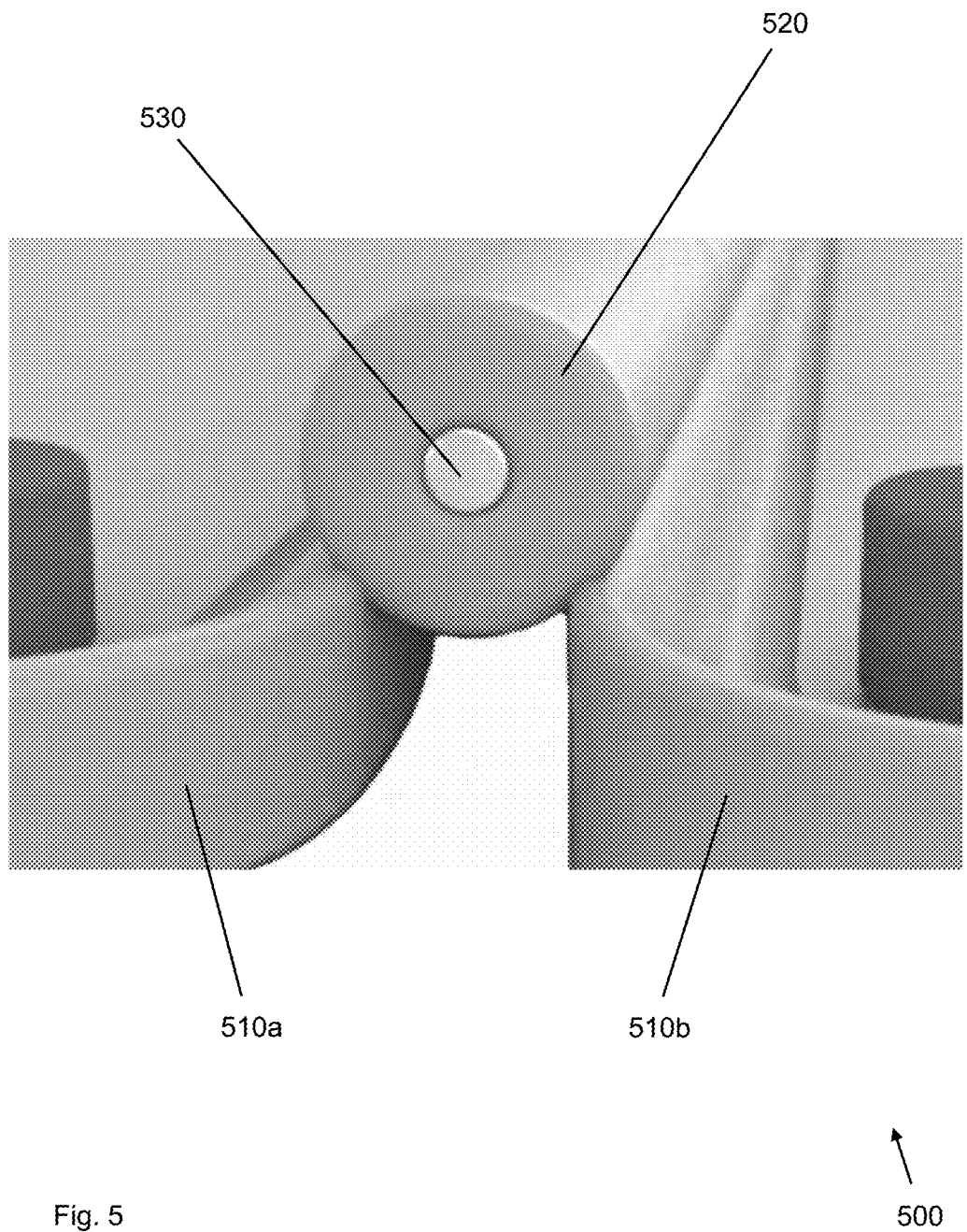
FIG. 5 illustrates a detailed view of a hinge portion of a sanitary medical surface device in an open configuration according to some embodiments of the present invention.

As shown in FIG. 5, a detailed view of a hinge portion of a sanitary medical surface device 500 in an open configuration is provided. The device 500 may comprise a first half portion 510a and a second half portion 510b coupled together via a rotatable hinge 520 having an elongate support member 530 running therethrough. The first and second half portions 510a, 510b may rotate between open and closed configurations via rotation of the hinge 520 about the elongate support member 530. The hinge 520 may comprise one or more sections that rotate relative one another but are kept in axial alignment along the axis defined by the elongate support member 530.

The one or more sections of the hinge 520 that rotate relative one another may provide the functionality that allows activation and deactivation of the antimicrobial illumination elements discussed in reference to FIG. 3. Specifically, each section of the hinge 520 may comprise a portion of the circuit between the power source and the antimicrobial illumination elements such that relative rotation between the hinge sections opens and closes the circuit depending upon the threshold rotation being crossed into the open or closed configurations.

Figure 6:
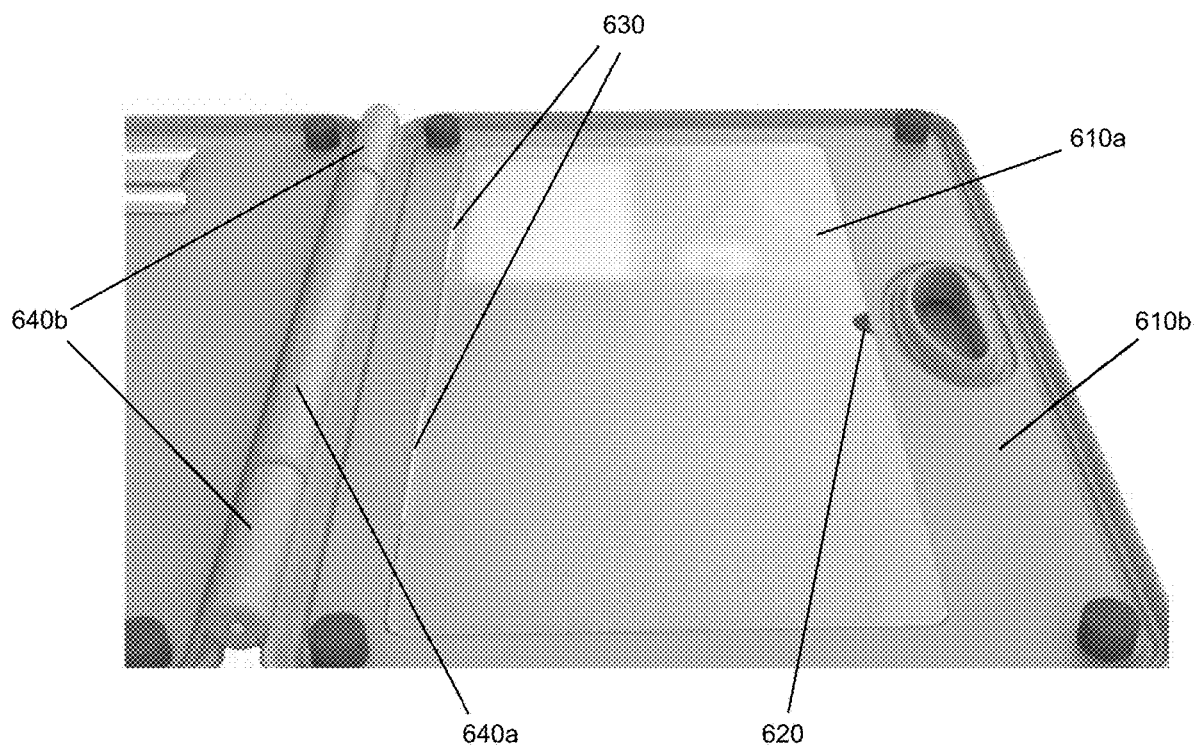
FIG. 6 illustrates an overview of a work surface of a portion of a sanitary medical surface device in an open configuration according to some embodiments of the present invention.

As shown in FIG. 6, an overview of a work surface of a portion of a sanitary medical surface device 600 in an open configuration is provided. The device 600 may comprise an inner work surface 610a that may be partially removable relative a remaining outer work surface 610b. Specifically, the inner work surface 610a may be rotated outward and away from the outer work surface 610b via one or more rotatable work surface hinges 630. Further, the in-home care nurse may manipulate the inner work surface 610a out from the stowed position via a tab or indent 620 which allows for grasping of the inner work surface 610a using the nurse's fingers.

Additionally, FIG. 6 illustrates the rotatable hinge having a first portion 640a and a second portion 640b that may be allowed to rotate relative one another to enable the device 600 to be rotated between the open and closed configurations. In some embodiments, the first rotatable hinge portion 640a may be coupled to either of the first half portion or the second half portion of the device 600 while the second rotatable hinge portion 640b may be coupled to whichever first or second half portion of the device 600 that the first rotatable hinge portion 640a is not coupled to. Thereby, each first and second half portion of the device 600 is securely coupled to the rotatable hinge and each first and second rotatable hinge portion 640a, 640b are free to rotate relative one another while still remaining axially aligned via the elongate support member discussed with reference to FIG. 5.

Figure 7:
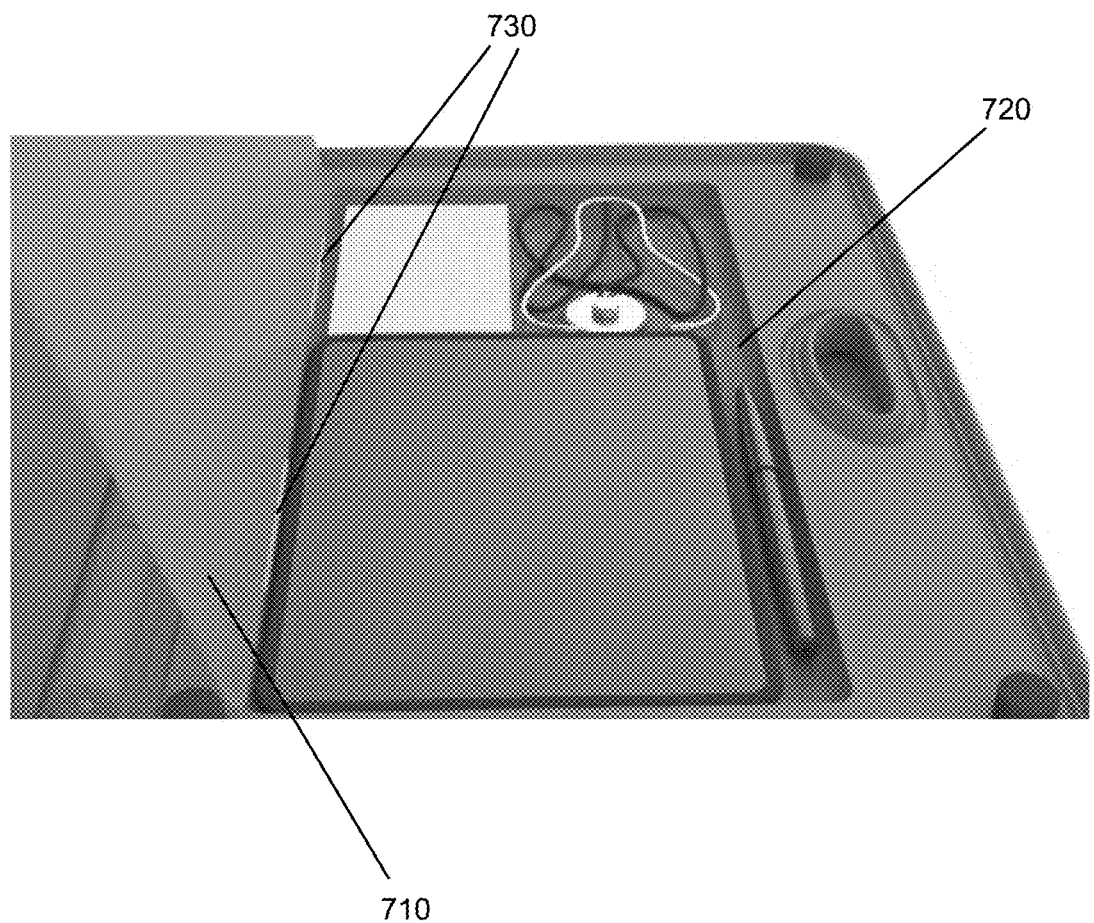
FIG. 7 illustrates an overview of a storage cavity disposed underneath a removable work surface of a portion of a sanitary medical surface device in an open configuration according to some embodiments of the present invention.

As shown in FIG. 7, an overview of a storage cavity disposed underneath a removable work surface of a portion of a sanitary medical surface device 700 in an open configuration is provided. The device 700 may comprise a partially removable inner work surface 710 that reveals a storage cavity 720 when rotated away via one or more rotatable work surface hinges 730. The storage cavity 720 may be utilized by the in-home care nurse to store therein medical equipment, medical supplies, administrative work equipment and the like or any combinations thereof. As shown in FIG. 7, a stethoscope, a tablet device, a writing utensil and a pad a paper may be stored within the storage cavity.

The storage cavity 720 may be designed to keep the contents stored therein stabilized during transport. If the contents are allowed to move around, then they may become structurally and/or functionally damaged and may create a jostling noise during transport that is undesirable to listen to during use. Advantageously, the storage cavity 720 may comprise one or more retention straps in order to secure contents within the cavity 720. The one or more retention straps may comprise coupling mechanisms that may take the form of hook and loop fastener patches, for example. Additionally, a structural recess may be formed into a bottom surface of the storage cavity 720 in order to retain one or more writing implements therein. Alternatively, the structural recess may extend from the bottom surface of the cavity 720 and may be defined by two walls extending therefrom to form the recess for retaining one or more writing implements. Further, the contents of the storage cavity 720 may further be secured therein by providing a locking and/or securement mechanism for the partially removable inner work surface 710 that acts as a lid for the cavity 720. The locking and/or securement mechanism may take the form of one or more magnets, clasps, clips and the like or any combination thereof that may be disposed upon any portion of the inner surface of the work surface 710 and/or on any portion of the exterior perimeter surface of the storage cavity 720.

Advantageously, the removable inner work surface 710 may form a fluid-tight seal with the remainder of the outer work surface of the device 700 when in the stowed configuration. The allows the equipment and supplies stored within the cavity 720 to remain free from contamination of any spilled liquid medical waste. Further, the fluid-tight seal across the work surface of the device 700 also creates a flush surface which is easily cleaned by the in-home care nurse between uses. Similarly, the one or more rotatable work surface hinges 730 may form a fluid-tight seal and flush surface with the entire work surface of the device 700.

Alternatively, the cavity 720 may only be accessible via a removable panel formed into one of the outer surfaces of the device 700 that enclose the inner surfaces when the device is in the closed configuration as shown in FIG. 1. Specifically, reference numeral 110 of FIG. 1 illustrates such an outer surface that may comprise the partially removable panel via one or more rotatable hinges that are described in association with FIGS. 6 and 7. Such a configuration may be advantageous over the inner surface removable panel of FIGS. 6 and 7 as any concerns about forming and maintaining a fluid-tight seal with the remainder of the work surface given the outer surface of the device would not be used as a work surface. Still, in such a configuration, the storage compartment may be fluidically sealed from environmental air, debris and other contaminants so as to keep the medical items therein in a sanitary state.

With reference to FIGS. 1-7, the sanitary medical surface device disclosed may comprise one or more closure locking mechanisms that secure the device when in the closed configuration. Further, any storage compartment accessible via an outer surface of the device may also be secured against opening when in the stowed configuration. For instance, one or more of magnets, clips, clasps and the like or any combination thereof may be utilized to secure the device into the closed configuration or the storage compartment in the stowed configuration.

With further reference to FIGS. 1-7, each of the work surfaces of the device may be fabricated from any suitable material that is structurally robust to typical items placed upon it in the practice of traveling medical professionals such as nurse practitioners, traveling nurses, hospice workers, therapists and the like. Further, an outer structural layer of each of the work surfaces may be fabricated from one or more hydrophobic materials, such as plexiglass, acrylic and the like, in order to prevent absorption of potentially hazardous medical waste fluids. Additionally or alternatively, the outer structural layer of each of the work surfaces may comprise one or more antimicrobial materials disposed therein and/or coated thereupon in order to prevent worksite contamination of the work surfaces by potentially hazardous pathogenic materials. Further, the antimicrobial materials may exhibit antiviral properties, antibacterial properties, antifungal properties and the like or any combination thereof. The material selected may also comprise a characteristic hardness value that is suitable for allowing a medical practitioner to hand-write upon each of the work surfaces. The device may be fabricated from a single unitary mold since the outer surfaces of the device could be fabricated from same material as the inner work surfaces, though the inner work surfaces may have one or more exterior layers coated or laminated thereupon after injection molding. Alternatively, each of the first and second half portions of the device may be individually injection molded and then coupled together via the hinges with other accessories assembled thereafter.

With further reference to FIGS. 1-7, the antimicrobial illumination elements may be powered via a solar panel and/or USB-type chargeable battery. The solar panel may be disposed into either of the outer surfaces of the first and/or second half portions of the device while the inner surfaces of the first and/or second half portions of the device may house the one or more antimicrobial illumination elements. It would be advantageous to utilize the solar panels on the outer surface so that solar charging may happen when the device is placed into the closed configuration and solar energy is incident thereupon during transport of the device between patient sites. Further, USB-type charging ports such as USB 1.0, USB 2.0, USB 3.0, USB-C and the like charging ports may be used to charge the battery that powers the antimicrobial illumination elements. Such a USB-type charging port may be disposed along any exterior surface of the device when in the closed configuration which would allow for wired charging of the battery when the device is not in use.

With further reference to FIGS. 1-7, each of the work surfaces may be utilized to perform typical medical service duties required by most medical professionals. Each of the work surfaces may further be utilized in a secondary manner as a writing surface, a fluid collection surface, a decontamination surface, a paper retention folder, a waste bag retention device and the like or any combination thereof. Additionally, each of the work surfaces of the device may be replaceable upon the exterior surfaces thereof becoming worn such that they lose their hydrophobic and/or antimicrobial properties.

With further reference to FIGS. 1-7, the first and second half portions may be utilized separately from one another such that they are not coupled together or may be utilized in combination with one another such that they are coupled together via the rotatable hinge. Moreover, the sanitary medical surface device may utilize only one of the first half portion or the second half portion in order to provide the in-home care nurse with an advantageous device to use while providing care to an in-home patient. Further, if the rotatable hinge is utilized, then the first half portion may be removably coupled to the second half portion via the rotatable hinge such that each of the first and second half portions may couple together and be decoupled from one another via the first and second hinge sections, respectively. The sanitary medical surface device may comprise only a first portion and may not utilize a second half portion or a hinge at all. The first portion embodiment of the sanitary medical surface device may be associated with all preceding disclosure related to the first half portion embodiments of the sanitary medical surface device.

The specification and drawings are to be regarded in an illustrative rather than a restrictive sense. However, it will be evident that various modifications and changes may be made thereunto without departing from the broader spirit and scope of the invention as set forth in the claims. Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

All features disclosed in the specification, claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

Throughout this disclosure, the phrase 'modularly coupled' and similar terms and phrases are intended to convey that any element of a given class of elements may be coupled to another given element and vice versa with equal effect. For example, any extension cord of a plurality of extension cords may be modularly coupled to another extension cord and vice versa with equal effect. Further, throughout this disclosure, the phrase 'removably coupled' and similar terms and phrases are intended to convey that a given element may be iteratively coupled to and removed from another given element as desired. For example, a male plug of a first extension cord may be removably coupled to a female plug of a second extension cord as desired.

The use of the terms "a," "an," "the," and similar referents in the context of describing the disclosed embodiments (especially in the context of the following claims) are to be construed to cover both the singular and the plural, unless otherwise indicated or clearly contradicted by context. The terms "comprising," "having," "including," and "containing" are to be construed as open-ended terms (i.e., meaning "including, but not limited to,") unless otherwise noted. The term "coupled" or "connected," where unmodified and referring to physical connections, is to be construed as partly or wholly contained within, attached to, or joined together, even if there is something intervening. Recitation of ranges of values are merely intended to serve as a shorthand method of referring individually to each separate value falling within the range, unless otherwise indicated and each separate value is incorporated into the specification as if it were individually recited. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Conjunctive language, such as phrases of the form "at least one of A, B, and C," or "at least one of A, B and C," is understood with the context as used in general to present that an item, term, etc., may be either A or B or C, or any nonempty subset of the set of A and B and C, unless specifically stated otherwise or otherwise clearly contradicted by context. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, the term "plurality" indicates a state of being plural (e.g., "a plurality of items" indicates multiple items). The number of items in a plurality is at least two, but can be more when so indicated either explicitly or by context.

The use of any examples, or exemplary language (e.g., "such as") provided, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described, including the best mode known to the inventors for carrying out the invention. Variations of those embodiments may become apparent to those of ordinary skill in the art upon reading the foregoing description. The inventors expect skilled artisans to employ such variations as appropriate and the inventors intend for embodiments of the present disclosure to be practiced otherwise than as specifically described. Accordingly, the scope of the present disclosure includes all modifications and equivalents of the subject matter recited in the claims appended hereto as permitted by applicable law. Moreover, although above-described elements may be described in the context of certain embodiments of the specification, unless stated otherwise or otherwise clear from context, these elements are not mutually exclusive to only those embodiments in which they are described; any combination of the above-described elements in all possible variations thereof is encompassed by the scope of the present disclosure unless otherwise indicated or otherwise clearly contradicted by context.

All references, including publications, patent applications, and patents, cited are hereby incorporated by reference to the same extent as if each reference were individually and specifically indicated to be incorporated by reference and were set forth in its entirety.

The invention claimed is:

1. A sanitary medical surface device, comprising:
  a first half portion which is coupled to a second half portion via a first rotatable hinge,
  wherein:
    the first half portion comprises a first outer surface and a first inner surface,
    the second half portion comprises a second outer surface and a second inner surface,
    the first inner surface or the second inner surface comprises a panel covering a storage compartment,
    the panel is partially removable via one or more second rotatable hinges to provide access to the storage compartment,
    the removable panel forms a fluid-tight seal with the first inner surface or the second inner surface, and
    the first inner surface comprises a first work surface and the second inner surface comprise a second work surface;
  a first channel depression formed into the first inner surface, wherein the first channel depression is disposed along first perimeter edges of the first work surface;
  a second channel depression formed into the second inner surface, wherein the second channel depression is disposed along second perimeter edges of the second work surface;
  a first raised lip disposed along third perimeter edges of the first inner surface;
  a second raised lip disposed along fourth perimeter edges of the second inner surface; and
  one or more stabilization structures disposed upon the first outer surface and the second outer surface.

2. The sanitary medical surface device of claim 1, wherein the first rotatable hinge comprises a first hinge section and a second hinge section.

3. The sanitary medical surface device of claim 1, wherein the first rotatable hinge rotates the first half portion relative the second half portion through an angle of no more than 180 degrees.

4. The sanitary medical surface device of claim 1, wherein, in a closed configuration, the first inner surface is disposed adjacent and parallel to the second inner surface and, in an open configuration, the first inner surface is disposed within the same plane as the second inner surface.

5. The sanitary medical surface device of claim 1, wherein a first portion of a handle cavity is disposed into the first outer surface and a second portion of the handle cavity is disposed into the second outer surface.

6. The sanitary medical surface device of claim 1, wherein the first inner surface or the second inner surface comprises a clip for retaining documents thereupon.

7. The sanitary medical surface device of claim 1, wherein the first inner surface or the second inner surface comprises a rounded retention depression formed therein.

8. The sanitary medical surface device of claim 1, wherein the panel forms a flush surface with the first inner surface or the second inner surface.

9. The sanitary medical surface device of claim 1, wherein the panel is the first work surface or the second work surface.

10. The sanitary medical surface device of claim 1, wherein the first inner surface comprises a third channel depression and the second inner surface comprises a fourth channel depression.

11. The sanitary medical surface device of claim 1, wherein a first handle aperture is disposed through the first outer surface and the first inner surface and a second handle aperture is disposed through the second outer surface and the second inner surface.

12. The sanitary medical surface device of claim 1, wherein each of the first and second channel depressions comprise a shape that tapers down in a rounded path from the first and second inner surfaces, respectively, towards a rounded bottom portion of the first and second channel depressions, respectively.

13. The sanitary medical surface device of claim 1, wherein each of the first and second channel depressions comprise a shape that forms a 90 degree angle squared-edge with the first and second inner surfaces, respectively.

14. A sanitary medical surface device, comprising:
  a first half portion and a second half portion coupled together via a first rotatable hinge,
  wherein:
    the first half portion comprises a first outer surface and a first inner surface and the second half portion comprises a second outer surface and a second inner surface,
    the first inner surface or the second inner surface comprises a panel covering a storage compartment,
    the panel is partially removable via one or more second rotatable hinges to provide access to the storage compartment,
    the removable panel forms a fluid-tight seal with the first inner surface or the second inner surface, and
    the first inner surface comprises a first work surface and the second inner surface comprise a second work surface;
  a first channel depression formed into the first inner surface, wherein the first channel depression is disposed along first perimeter edges of the first work surface;
  a second channel depression formed into the second inner surface, wherein the second channel depression is disposed along second perimeter edges of the second work surface;
  a first raised lip disposed along third perimeter edges of the first inner surface and a second raised lip disposed along fourth perimeter edges of the second inner surface;
  a first handle aperture disposed through the first outer surface and the first inner surface and a second handle aperture disposed through the second outer surface and the second inner surface, wherein a third channel depression is formed into the first inner surface and disposed around the first handle aperture and a fourth channel depression is formed into the second inner surface and disposed around the second handle aperture; and one or more stabilization structures disposed upon either or both of the first outer surface and the second outer surface.

15. A sanitary medical surface device, comprising:

a first half portion and a second half portion coupled together via a first rotatable hinge, wherein:
- the first half portion comprises a first outer surface and a first inner surface and the second half portion comprises a second outer surface and a second inner surface,
- the first inner surface or the second inner surface comprises a panel covering a storage compartment,
- the panel is partially removable via one or more second rotatable hinges to provide access to the storage compartment,
- the removable panel forms a flush surface with the first inner surface or the second inner surface, and
- the first inner surface comprises a first work surface and the second inner surface comprise a second work surface;

a first channel depression formed into the first inner surface, wherein the first channel depression is disposed along first perimeter edges of the first work surface;

a second channel depression formed into the second inner surface, wherein the second channel depression is disposed along second perimeter edges of the second work surface;

a first raised lip disposed around the first channel depression and a second raised lip disposed around the second channel depression; and a plurality of stabilization structures disposed upon each of the first outer surface, the first inner surface, the second outer surface and the second inner surface.

* * * * *